(12) United States Patent
Boutignon (10) Patent No.: US 6,627,600 B2
(45) Date of Patent: Sep. 30, 2003

(54) COMPRESSED MICROPARTICLES FOR DRY INJECTION

(75) Inventor: Francois Boutignon, Ermont (FR)

(73) Assignee: Ardana Bioscience Limited, Edinburgh (GB)

( * ) Notice: Subject to any disclaimer, the term of this patent is extended or adjusted under 35 U.S.C. 154(b) by 0 days.

(21) Appl. No.: 09/764,111

(22) Filed: Jan. 19, 2001

(65) Prior Publication Data

US 2001/0026804 A1 Oct. 4, 2001

Related U.S. Application Data

(63) Continuation-in-part of application No. 09/491,978, filed on Jan. 27, 2000, now abandoned.

(51) Int. Cl.$^7$ .......................... A61K 38/00; A61K 9/00; A61K 47/00
(52) U.S. Cl. .......................... 514/2; 424/422; 424/423; 424/424; 424/425; 424/426; 424/490; 424/497; 424/499; 424/501; 514/769; 514/772; 514/772.3; 514/772.5; 514/772.7; 514/777; 514/778; 514/781; 514/784; 514/953; 514/965
(58) Field of Search .............................. 424/422, 423, 424/424, 425, 426, 490, 497, 499, 501; 914/2, 769, 772, 772.3, 772.5, 772.7, 777, 778, 781, 784, 953, 965

(56) References Cited

U.S. PATENT DOCUMENTS

| | | | |
|---|---|---|---|
| 3,887,699 A | 6/1975 | Yolles | 424/19 |
| 4,351,337 A | 9/1982 | Sidman | 128/260 |
| 4,384,005 A | 5/1983 | McSweeney | 426/250 |
| 4,652,441 A | 3/1987 | Okada et al. | 424/19 |
| 4,728,721 A | 3/1988 | Yamamoto et al. | 528/361 |
| 4,761,289 A | 8/1988 | Shalati et al. | 424/468 |
| 4,849,228 A | 7/1989 | Yamamoto et al. | 424/457 |
| 4,863,743 A * | 9/1989 | Hsiao et al. | 424/476 |
| 4,917,893 A | 4/1990 | Okada et al. | 424/423 |
| 4,954,298 A | 9/1990 | Yamamoto et al. | 264/4.6 |
| 5,023,082 A | 6/1991 | Friedman et al. | 424/426 |
| 5,330,767 A | 7/1994 | Yamamoto et al. | 424/497 |
| 5,342,622 A | 8/1994 | Williams et al. | 424/425 |
| 5,470,311 A | 11/1995 | Setterstrom et al. | 604/24 |
| 5,476,663 A | 12/1995 | Okada et al. | 424/423 |
| 5,480,656 A | 1/1996 | Okada et al. | 424/493 |
| 5,486,362 A | 1/1996 | Kitchell et al. | 424/426 |
| 5,574,011 A * | 11/1996 | Tien | 514/14 |
| 5,575,987 A | 11/1996 | Kamei et al. | 424/451 |
| 5,631,021 A | 5/1997 | Okada et al. | 424/451 |
| 5,643,607 A | 7/1997 | Okada et al. | 424/493 |
| 5,716,640 A | 2/1998 | Kamei et al. | 424/451 |
| 5,744,163 A | 4/1998 | Kim et al. | 424/489 |
| 5,766,631 A | 6/1998 | Arnold | 424/486 |
| 5,945,128 A | 8/1999 | Deghenghi | 424/501 |
| 6,506,785 B2 * | 1/2003 | Evans et al. | 514/411 |

FOREIGN PATENT DOCUMENTS

| | | |
|---|---|---|
| EP | 052510 | 5/1982 |
| WO | WO 01/37811 | 5/2001 |

OTHER PUBLICATIONS

Mirriam–Webster's Collegiate Dictionary (10th Ed. 1998), pp. 431, 435.*

Jeffrey D. Meyer et al., "Preparation and in Vitro Characterization of Gentamycin–Impregnated Biodegradable Beads Suitable for Treatment of Osteomyelitis", *J. of Pharmaceutical Sciences*, vol. 87, No. 9, Sep. 1998, pp. 1149–1154.

A. Kader and R. Jalil, "Formulation factors Affecting Drug Release from Poly(Lactic Acid) (PLA) Microcapsule Tablets", Drug Development and Industrial Pharmacy, 25(2) 1999, pp. 141–151.

Murakami, H. et al., "Utilization of poly(dl–lactide–co–glycolide) nanoparticles for preparation of mini–depot tablets by direct compression," *Journal of Controlled Release 67*, pp. 29–36, 2000.

* cited by examiner

*Primary Examiner*—Michael G. Hartley
*Assistant Examiner*—Frank Choi
(74) *Attorney, Agent, or Firm*—Winston & Strawn LLP (57) ABSTRACT

The invention relates to a pharmaceutical implant for controllably releasing a drug in a subject and methods for manufacturing and administering the implant. The implant is made of associated microparticles of a drug dispersed in a biodegradable polymer. The microparticles are sufficiently associated so that the implant maintains a predetermined shape but are not fused together so as to form a single monolithic structure. The drug can be controllably released in a subject by administration of the pharmaceutical implant without the need of a suspending fluid.

41 Claims, 9 Drawing Sheets

COMPRESSED MICROPARTICLES FOR DRY INJECTION

This is a continuation-in-part of application Ser. No. 09/491,978 filed Jan. 27, 2000, now abandoned.

TECHNICAL FIELD

The present invention relates to an implant made of compacted microparticles and a method of manufacturing the compacted microparticles. The invention also relates to a method of administering such compacted microparticles to a subject.

BACKGROUND ART

In the administration of drugs and in the diagnosis of disease it is desirable, if not necessary, to effect a controlled release of one or more substances within the living organism, in particular within a mammal, over an extended period of time.

Controlled release over an extended period of time, however, is not possible by conventional methods of administering drugs such as oral administration or direct injection of a drug. Rather than providing a controlled concentration of the drug over an extended period of time, these methods of administration lead to an immediate release of the drug into the body followed by a decline in the blood level of the drug over time. The immediate release of drug, followed by a decline in the blood level of the drug over time, is often not the most desirable method of administration. Treatment of a disease or condition is often more effective when the level of the drug in the blood can be maintained at a desired constant level for an extended period of time. Moreover, the immediate entry of a drug into a body may create a concentration of the drug beyond the capacity of the active centers to accept the drug and may also exceed the capacity of the metabolic and excretory mechanisms of the living organism. If the level of the drug remains elevated, tissues and/or organs may suffer detrimental effects.

Continuous controlled release of a drug over an extended period of time has significant clinical advantages as well. For example, when drug treatment must continue for an extended period of time, oral administration or direct injection requires the inconvenience of repeated administration. Furthermore, when the treatment requires repeat administration there is the possibility that the patient will forget or purposely not administer the drug. If a drug can be administered in a continuous, controlled release manner over an extended period of time the need for repeat administration is avoided.

To achieve a desired blood level of a drug over an extended period of time a variety of implants have been developed that, when administered to a patient, provide continuous, controlled release, long term delivery of a drug. These formulations include dosage forms intended for ingestion, injection, vaginal and uterine insertion, percutaneous application, and subcutaneous implants, for example.

The implants contain the active agent or drug in combination with a polymeric delivery system that controls release of the drug. The drug is physically entrapped in the polymer matrix and is released from the matrix by diffusion through the polymer or breakdown of the polymer matrix. Typically, the polymeric delivery system is a biocompatible, biodegradable polymer matrix. The polymer matrix is, however, not always biodegradable. When non-biodegradable implants are used surgical removal of the implant is necessary after the drug has been released.

A number of matrix materials gave been developed for controlled release of drugs including polymer matrix materials made of hydrogels, gelatin, cellulose, organopolysiloxane rubbers, polyurethanes, waxes, polyvinyl alcohol, poly glycolic acid, and polylactic acid, for example. Frequently the polymer matrix is a copolymer of lactic acid and glycolic acid ("PLGA", polylactic glycolic acid). Drug is released from the PLGA matrix by the hydrolytic breakdown of the matrix. As the polymeric matrix breaks down the drug is released into the surrounding body fluids.

The rate of drug delivery is affected by a variety of variables including, for example, the choice of the polymer matrix, concentration of the drug in the matrix, size and shape of the implant, method of manufacturing the implant, surface area of the implant, and pore size.

Microparticles are an example of a sustained release formulation, wherein the drug is administered in connection with a polymeric delivery system. Microparticles are fine particles of drug physically entrapped in the polymer matrix. The microparticles can be prepared by a variety of methods such as the phase separation method, described in European Patent No. 52,510, or by preparing a water-in-oil emulsion as described in U.S. Pat. No. 4,652,441 to Okada et al. Typically, the particle size is in the range of 0.5 to 400 $\mu$m. The microparticles may be included in injections, oral preparations (powders, granules, capsules, tablets, etc.), nasal preparations, suppositories (e.g., rectal, vaginal) and so on. The drug is released in a controlled manner by degradation of the polymer matrix.

Microparticles are most commonly administered by injection. An injectable preparation of the microparticles is prepared by suspending the microparticles in a suitable fluid. Suspending microparticles in a suitable fluid, however, is problematic in that the microparticles often tends to flocculate or clump together. Thus, preparing the injectable suspension must be done properly and carefully and can be a very tedious process. In addition, material is often lost when the suspension of microparticles is drawn into the syringe. Yet another disadvantage of administering microparticles by injection is that the administration is associated with a "burst" or an immediate release of the drug over a short period of time, followed by a slower more uniform release. The burst precludes high core loading of the microparticles (the concentration of the active principal within the microparticles) because the burst increases with core loading. Therefore, in order to inject a certain amount of drug, one must inject a high quantity of material having a low core loading and, thus, a large volume of suspension fluid.

Subcutaneous implants are another example of a sustained release formulation, wherein the drug is administered in connection with a polymeric delivery system. Subcutaneous implants are solid bodies containing drug physically entrapped in a polymer matrix. The solid body is much larger than microparticles and is implanted under the patients skin either surgically or by sub-dermal injection using conventional implanting devices. The implants may have a variety of shapes including a film, rod, fiber, hollow cylinder, closed tube, and the like.

The subcutaneous implants are manufactured by first forming a mixture of the drug and polymer matrix and then forming the implant, of desired structural shape, by injection molding, compression molding, or extruding the resulting mixture to produce a solid, uniform, monolithic implant. The mixture of drug and polymer matrix is formed either by mixing the drug with the dry polymeric material in powdered form or by forming a solution or slurry of the drug and polymer and removing the solvent.

Subcutaneous implants, however, often do not provide continuous, uniform release of the drug and may exhibit a "burst" or a "dead phase" following administration. The "dead phase" is a period during which essentially no active ingredient is released.

Yet another implant device for continuous release of actives are osmotic mini-pumps. Osmotic mini-pumps are, however, expensive and require surgical implantation and removal.

The prior art discloses a number of delayed release polymer/drug formulations, including the following:

U.S. Pat. No. 3,887,699 to Yolles discloses an article for dispensing drugs prepared by dispersing a drug in a biodegradable polymeric material that can be formed into a solid shape. Drug is released when the drug migrates or exudes from the interior to the surface of the polymeric article and/or when the polymer degrades.

U.S. Pat. No. 4,351,337 to Sidman discloses a biocompatible, biodegradable implant device formed as a structure in which a drug or other releaseable substance to be delivered is physically contained by a poly-α-amino acid.

U.S. Pat. No. 4,761,289 to Shalati et al. describes a method for preparing a sustained release pellet for use as an implant. The pellet, containing a water insoluble polymer and a water diffusible solid, is prepared by forming a mixture comprising a dispersion of a water diffusible solid in a solution of a non-aqueous solvent and a water insoluble polymer, removing the non-aqueous solvent from the mixture to substantially dry the mixture, comminuting the substantially dry mixture to form substantially dry particles, and forming a plurality of the substantially dry particles under pressure into a pellet. The process provides a homogenous implant. Diffusion of the diffusible solvent as body fluids gradually penetrate the pellet.

U.S. Pat. No. 5,023,082 to Friedman et al. discloses a sustained release composition that is suitable for implantation in the periodontal crevice for the treatment of periodontal disease.

U.S. Pat. No. 5,342,622 to Williams et al. discloses subdermally administered pharmaceutical veterinary implants for continuous release of a peptide or protein. The implant includes a peptide or protein and an excipient encased within a polymeric coating which is permeable, swellable, and, at normal physiological pH, is non-rupturing, non-dissolving, and does not degrade over the useful life of the implant.

U.S. Pat. No. 5,470,311 to Setterstrom et al. discloses an apparatus for dispensing micro encapsulated medicinal compositions. The apparatus generates a nebulizing gas stream that sprays or propels powdered microspheres, contained in a vial, into or onto an area to be treated as a stream.

U.S. Pat. No. 5,486,362 to Kitchell et al. discloses a method for treating individuals for drug dependence and a drug delivery system useful for treating drug dependence. The method comprises administering a therapeutic level of a drug substitute in a controlled, sustained release manner over a period of time having a duration of at least one day. The drug delivery system uses a physical constraint modulation system ("PCMS") to contain the drug substitute. The PCMS may be a biodegradable polymer. The formulation of the biodegradable polymer and drug substitute may be suitable for subcutaneous or intramuscular injection and includes microparticles, microcapsules, and elongated rods of the polymer/drug substitute.

U.S. Pat. Nos. 4,652,441; 4,917,893; 5,476,663; and 5,631,021 to Okada et al. describe a prolonged release microcapsule and a process for producing the microcapsule.

U.S. Pat. Nos. 4,728,721 and 4,849,228 to Yamamoto et al. describe a biodegradable high molecular weight polymer useful as an excipient in producing pharmaceutical preparations, a method of producing the polymer, and microcapsules produced from the polymer.

U.S. Pat. Nos. 4,954,298 and 5,330,767 to Yamamoto et al. describe a sustained-release microcapsule for injection containing a water-soluble drug and a method for producing the microcapsules.

U.S. Pat. Nos. 5,480,656 and 5,643,607 to Okada et al. describe a microcapsule designed for zero order release of a physiologically active peptide over a period of at least two months.

U.S. Pat. No. 5,744,163 to Kim et al. describes a sustained released formulation of an animal growth hormone and a process for manufacturing the formulation. The process involves forming a mixture of hormone and excipient into a tablet using conventional tabletting methods and then coating the tablet with a polymer film.

U.S. Pat. Nos. 5,575,987 and 5,716,640 to Kamei et al. describe sustained-release microcapsules containing a biologically active substance adapted to release the biologically active substance at a constant rate over a protracted time starting immediately following administration without an initial burst and a method of producing the sustained-release microcapsules.

J. D. Meyer et al. in an article entitled "Preparation and In Vitro Characterization of Gentamycin-Impregnated Biodegradable Beads Suitable for Treatment of Osteomyelitis" in the Journal of Pharmaceutical Sciences, vol. 67, no. 9, September, 1998 describe implantable beads containing 6.7 percent gentamycin that are strung on a surgical suture and implanted in a wound following surgery. The beads are formed by compressing dry microparticles having a diameter of approximately 1 $\mu$m. The microparticles are formed by a process that involves first solubilizing the drug molecule in an appropriate solvent using a process called hydrophobic ion pairing (HIP) and then forming the microspheres using a method termed precipitation with a compressed antisolvent (PCA). The beads exhibit drug release that is consistent with a matrix controlled diffusion.

A. Kader et al. In an article entitled "Formulation Factors Affecting Drug Release from Poly(Lactic)Acid (PLA) Microcapsule Tablets" in Drug Development and Industrial Pharmacy, 25(2), 141–151, 1999 describe tablets of compacted microparticles for oral ingestion and oral drug delivery. Compaction results in tablets that are intact tablets or in tablets that disintegrate in the gastrointestinal tract. The disintegration of the tablets is influenced by compression pressure and added excipients.

There remains a need, however, for improved implants and improved methods for administering drugs and other substances in a continuous, controlled manner over an extended period of time. The present invention provides such an implant and methods.

SUMMARY OF THE INVENTION

The present invention relates to a pharmaceutical implant for controllably releasing a drug in a subject. The pharmaceutical implant includes microparticles of one or more drugs dispersed in a biodegradable polymer, wherein the microparticles are sufficiently associated to maintain a predetermined shape of the implant without complete fusing of the polymer and wherein the implant disintegrates into individual microparticles over time after administration.

The amount of the drug can be between about 0.5 to 95 percent (w/w) of the microparticles. Preferably, the amount of the drug is between about 5 to 75 percent (w/w) of the microparticles.

The biodegradable polymer can be a polymer of lactic acid, glycolic acid, polyethylene glycol, poly(ortho esters), poly caprolacatones, or copolymers thereof.

The pharmaceutical implant may further include one or more additives. The additives may be biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucuronic acid, gluconic acid, polysorbate, sodium acetate, sodium citrate, sodium phosphate, zinc stearate, aluminum stearate, magnesium stearate, sodium carbonate, sodium bicarbonate, sodium hydroxide, polyvinylpyrrolidones, polyethylene glycols, carboxymethyl celluloses, methyl celluloses, starch, or a mixture thereof.

The pharmaceutical implant can have a cylindrical shape with a diameter between about 0.5 to 5 mm, and a length of between about 0.5 to 10 cm. Preferably, the diameter is between about 1 to 3 mm and a length of between about 1 to 5 cm.

The invention also relates to a method for controllably releasing a drug in a subject by administering to the subject a pharmaceutical implant including microparticles of one or more drugs dispersed in a biodegradable polymer, wherein the microparticles are sufficiently associated to maintain a predetermined shape of the implant without complete fusing of the polymer and wherein the implant disintegrates into individual microparticles over time after administration. The implant can be administered intramuscularly or subcutaneously and may be administered surgically or by using an implantation device. The implantation device may be pre-filled with the implant.

The invention further relates to methods of preparing a pharmaceutical implant for controllably releasing a drug in a subject. One embodiment of the method involves the steps of: placing microparticles of one or more drugs dispersed in a biodegradable polymer in a forming zone defined by a vessel having an upper end and a lower end, wherein the upper end has an opening to permit the microparticles and a fluid to be introduced into the forming zone, the lower end is covered with a seal that prevents the microparticles from exiting the forming zone but allows gases and fluids to exit the forming zone; adding a fluid to the upper end of the forming zone in an amount sufficient to evenly coat the microparticles to increase adhesion of the microparticles; applying a pressure to the upper end of the forming zone to compact the microparticles and sufficiently associate the microparticles so that they maintain the shape of the forming zone without complete fusing of the polymer; removing the compacted microparticles from the forming zone in the shape of the implant; and drying the compacted microparticles to provide a pharmaceutical implant that disintegrates into individual microparticles over time after the implant is administered to a subject.

The method may also include adapting the lower end of the forming zone to receive a vacuum and applying a vacuum to the lower end of the forming zone, after the fluid is added, to evenly coat the microparticles with the fluid. The vacuum may create a reduced pressure of between about 2 and 50 inches of mercury.

A second embodiment of the method involves the steps of: combining microparticles of one or more drugs dispersed in a biodegradable polymer with a fluid to form a wet granulate; placing the wet granulate in a forming zone defined by a vessel having an upper end and a lower end, wherein the upper end permits the wet granulate to be introduced into the forming zone and the lower end prevents the microparticles from exiting the forming zone; applying pressure to the upper end of the forming zone to compact the microparticles and sufficiently associate the microparticles so that they maintain the shape of the forming zone without complete fusing of the polymer; removing the compacted microparticles from the forming zone in the shape of the implant; and drying the compacted microparticles to provide a pharmaceutical implant that disintegrates into individual microparticles over time after the implant is administered to a subject.

The applied pressure is from about 1 $kg/cm^2$ and 1,000 $kg/cm^2$. The pressure is applied for between about 1 second to 10 minutes. The upper end of the forming zone may be adapted to receive a plunger and the pressure applied using the plunger.

The microparticles may be combined with one or more additives to form a mixture before placing the mixture in the forming zone. Similarly the wet granulate may be combined with one or more additives before placing the wet granulate in the forming zone. The additives can be biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucoronic acid, gluconic acid, polysorbate, sodium acetate, sodium citrate, sodium phosphate, zinc stearate, aluminum stearate, magnesium stearate, monobasic sodium, sodium carbonate, sodium bicarbonate, sodium hydroxide, polyvinylpyrrolidones, polyethylene glycols, carboxymethyl celluloses, methyl celluloses, starch, or a mixture thereof. The additive, when present, is present in an amount of between about 0.05 percent (w/w) and 75 percent (w/w) of the implant.

The fluid is added in an amount of between about 20 percent (v/w) and 200 percent (v/w) of the weight of the microparticles. The fluid can be one or more of water, ethanol, methanol, or heptane. A solute may also be added to the one or more fluids. The solute may be mannitol, a salt, polyethylene glycol, an acid, a base, or a mixture thereof.

The compacted microparticles may be dried at a temperature of between about 15° C. to 40° C. The compacted microparticles may be dried under reduced pressure or in the presence of a desiccant.

DETAILED DESCRIPTION OF THE PREFERRED EMBODIMENTS

The present invention is directed at an injectable sustained release formulation in the form of an implant. The implant is made up of compacted microparticles that, after administration to a patient, continuously release a drug in a controlled manner for an extended period of time. The invention is also directed to a method of administering a drug to a subject over an extended period of time in a controlled release manner by administering to the subject an implant made of compacted microparticles. The invention is also directed to a process for manufacturing the implant of compacted microparticles.

The implant of the present invention is made up of microparticles that have been compacted together under pressure. Thus, the microparticles that make up the implant are not free flowing but are sufficiently associated so that the implant can maintain a pre-determined shape. The compacted microparticles, however, remain as individual particles and are not fused together. Thus, the implant of the invention differs from conventional implants formed by injection molding, compression molding, or extrusion that results in the polymer melting and fusing into a single monolithic structure.

By microparticle is meant a particle comprising a drug physically entrapped in a polymer matrix and having a particle size less than about 1,000 microns. The microparticles may be microspheres, microcapsules, or microgranules. By microsphere is meant a spherical microparticle where the drug is uniformly dissolved or entrapped in the matrix lattice. By microcapsule is meant a spherical microparticle where the drug is encapsulated by a polymer membrane. By microgranule is meant an irregularly shaped microparticle where the active ingredient is uniformly dissolved or entrapped in the matrix lattice. The size of the microparticles are between about 1 micron and 1,000 microns, preferably between about 10 microns and 500 microns, and more preferably between about 50 microns and 250 microns.

The term drug is meant to include all substances that effect some biological response. The term drug encompasses drugs useful to any mammal including but not limited to human beings, household animals, wild animals, and animals raised for their meat or other products such as farm animals and cattle. The term drug includes, but is not limited to the following classes of drugs: therapeutic drugs, preventative drugs, and diagnostic drugs. Examples of drugs that can be incorporated into the polymer matrix include, but are not limited to: narcotic pain relievers; gold salts; corticosteroids; hormones; anti-malarials; indole derivatives; drugs for the treatment of arthritis; antibiotics including tetracyclines, penicillin, streptomycin, and aureomycin; deworming and distemper drugs such as those given to household pets and cattle of which phenothiazine is an example; sulfur drugs such as sulfisoxazole; anti-tumor drugs, addiction-control agents such as alcohol-addiction control agents and tobacco-addiction control agents; addictive drug antagonists such as methadone; weight-control drugs; thyroid gland regulating drugs; analgesics; hormone regulating drugs to aid in fertilization or contraception; amphetamines; antihypertensive drugs; anti-inflammatory agents; antitussives; sedatives; muscle relaxants; antiepileptics; antidepressants; antiarrhythmic agents; vasodilators; antihypertensive diuretics; antidiabetic agents; anticoagulants; antitubercular agents; agents for treating psychosis; hormones; and peptides. The above list is not meant to be comprehensive and is merely representative of the wide variety of drugs that may be incorporated into the microparticles. Preferably the drug is a peptide.

The amount of drug dispersed in the polymeric matrix will depend on a variety of factors including, for example, the specific drug, the function to be accomplished, the length of time it is desired to release the drug, the amount of drug to be administered, and the size of the implant. Typically core loading of the drug, i.e., the concentration of the drug in the microparticles, ranges from about 0.5 to 95% (w/w), preferably from about 5% to 75% (w/w), and more preferably from about 10% to 60% (w/w).

The polymer matrix is a biodegradable biocompatible polymer. The term biodegradable means any material that is degradable in vivo where the material is broken down into simpler chemical species which are either eliminated or metabolized. The term biocompatible means any material that does not produce a toxic, injurious, or immunological response in living tissue. Examples of biodegradable polymers include, but are not limited to, aliphatic polymers (e.g., polylactic acid, polyglycolic acid, polycitric acid, and polymalic acid), poly-α-cyanoacrylic acid esters, poly β-hydroxybutyric acid, polyalkylene oxalate (e.g., polytrimethylene oxalate and polytetramethylene oxalate), polyorthoesters, polyorthocarbonates and other polycarbonates (e.g., polyethylene carbonate and polyethylenepropylene carbonate), polyamino acids (e.g., poly-γ-benzyl-L-glutamic acid, poly-L-alanine, poly-γ-methyl-L-glutamic acid), polystyrene, polyacrylic acid, polymethacrylic acid, acrylic acid-methacrylic acid copolymers, polyamides (nylon), polyethylene terephthalate (tetron), polyamino acids, silicon polymers, dextran stearate, ethylcellulose, acetylcellulose, nitrocellulose, polyurethanes, maleic anhydride-based copolymers, polyvinyl acetate, polyvinyl alcohol, and polyacrylamide. The polymer may be a homopolymer or copolymer of two or more monomers, or a mixture of polymers, and may also be in the salt form. Preferred polymers are polymers of lactic acid, glycolic acid, polyethylene glycol, poly(ortho esters), poly caprolacatones, and copolymers thereof.

In addition to the compacted microparticles the implant may also include one or more additives such as biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucuronic acid, gluconic acid, polysorbate, sodium acetate, sodium citrate, sodium phosphate, zinc stearate, aluminum stearate, magnesium stearate, sodium carbonate, sodium bicarbonate, sodium hydroxide, polyvinylpyrrolidones, polyethylene glycols, carboxymethyl celluloses, methyl celluloses, starch, and the like, or mixtures thereof. These other materials increase or slow down disintegration of the implant as a result of their acidic or basic properties; hydrophobic properties; hydrophilic properties; and their ability to swell, or lubricate.

The implant may have any shape including, but not limited to a film, a sphere, a fiber, a pellet, or a cylinder. Preferably the implant is a cylinder. The size of the cylinder can be between about 0.5 and 5 mm in diameter and 0.5 to 10 cm in length, preferably, between about 1 and 3 mm in diameter and 1 to 5 cm in length.

The present invention is further directed at a process for administering microparticles to a subject. The method involves administering the microparticles as an implant made up of compacted microparticles either intramuscularly or subcutaneously. The implant of compacted microparticles can be administered by any method known to those of ordinary skill in the art including surgical implantation or using an implantation device. Implantation devices are well known to those of ordinary skill in the art and need not be discussed here. Preferably, the implant of compacted microparticles is administered using a syringe with a retractable needle. In a more preferred embodiment the syringe with a retractable needle is pre-filled with the implant.

Figures 1A, 1B:
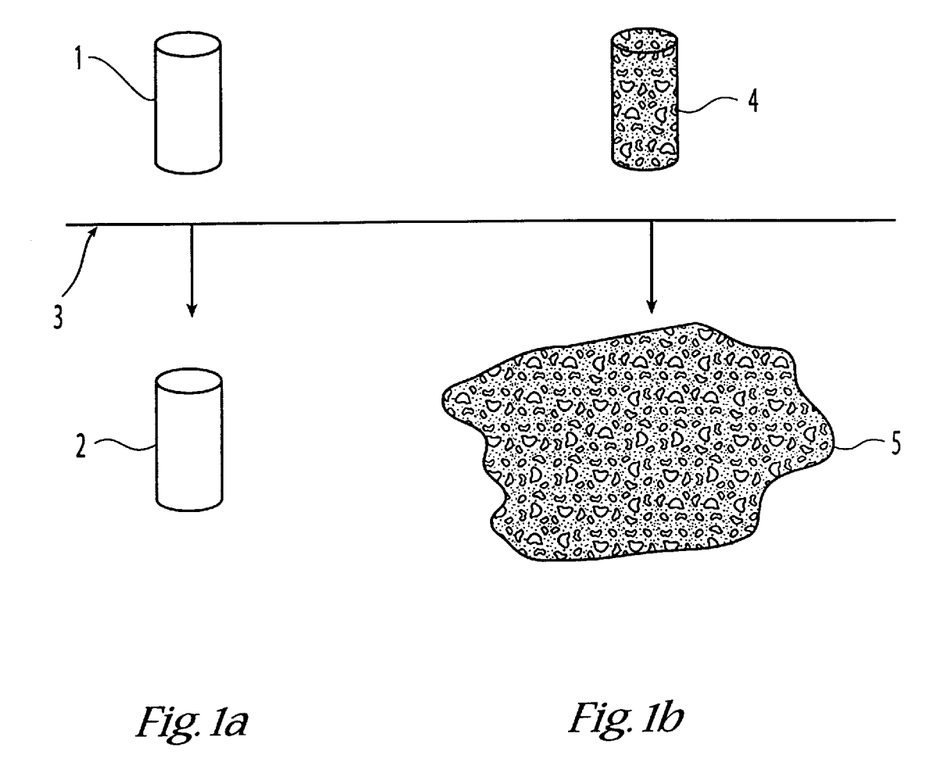
FIG. 1 is a schematic depicting the different behavior of a monolithic implant and an implant according to the present invention soon after the implants are injected under the skin.

The implant of the invention differs from a conventional subcutaneous implant in that a conventional subcutaneous implant remains as a single monolithic implant after administration under the skin. In contrast, the implant of the present invention, not being a monolithic implant but being individual particles compacted together, disintegrates into the individual microparticles after it is implanted under the skin. The difference in behavior between a conventional monolithic implant and the implant of the invention after injection is depicted in FIG. 1. FIG. 1a shows a conventional monolithic implant before injection (1) and soon after injection (2) under the skin (3). FIG. 1b shows an implant according to the invention before injection (4) and soon after injection (5) under the skin (3).

Administering microparticles according to the method of the present invention, i.e., as an implant of compacted microparticles, avoids the difficulties associated with administering them as a suspension. The present method is a single step injection that does not require a suspension fluid and thus avoids the tedious steps necessary to prepare the suspension and avoids mechanical loss of the microparticles when the suspension is withdrawn into a syringe. Furthermore, administering the drug as compacted microparticles, rather than as a suspension, provides better control of the burst, since some drug is inevitably dissolved in the suspension fluid.

Figure 2:
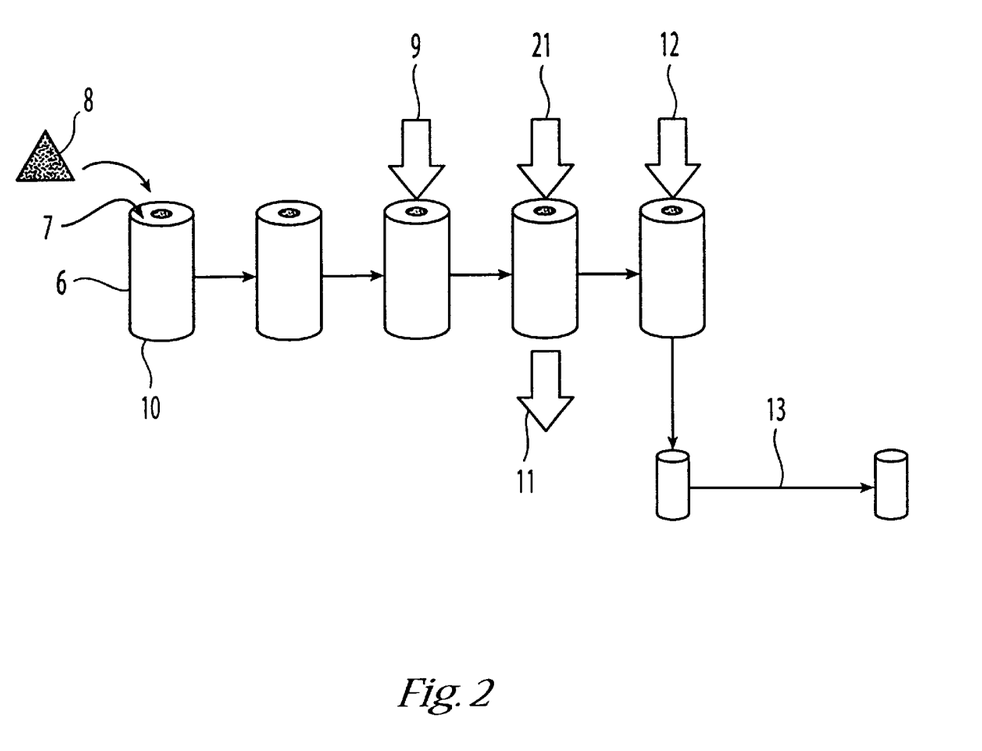
FIG. 2 is a schematic representation of a process for manufacturing an implant according to the present invention.
Figure 3:
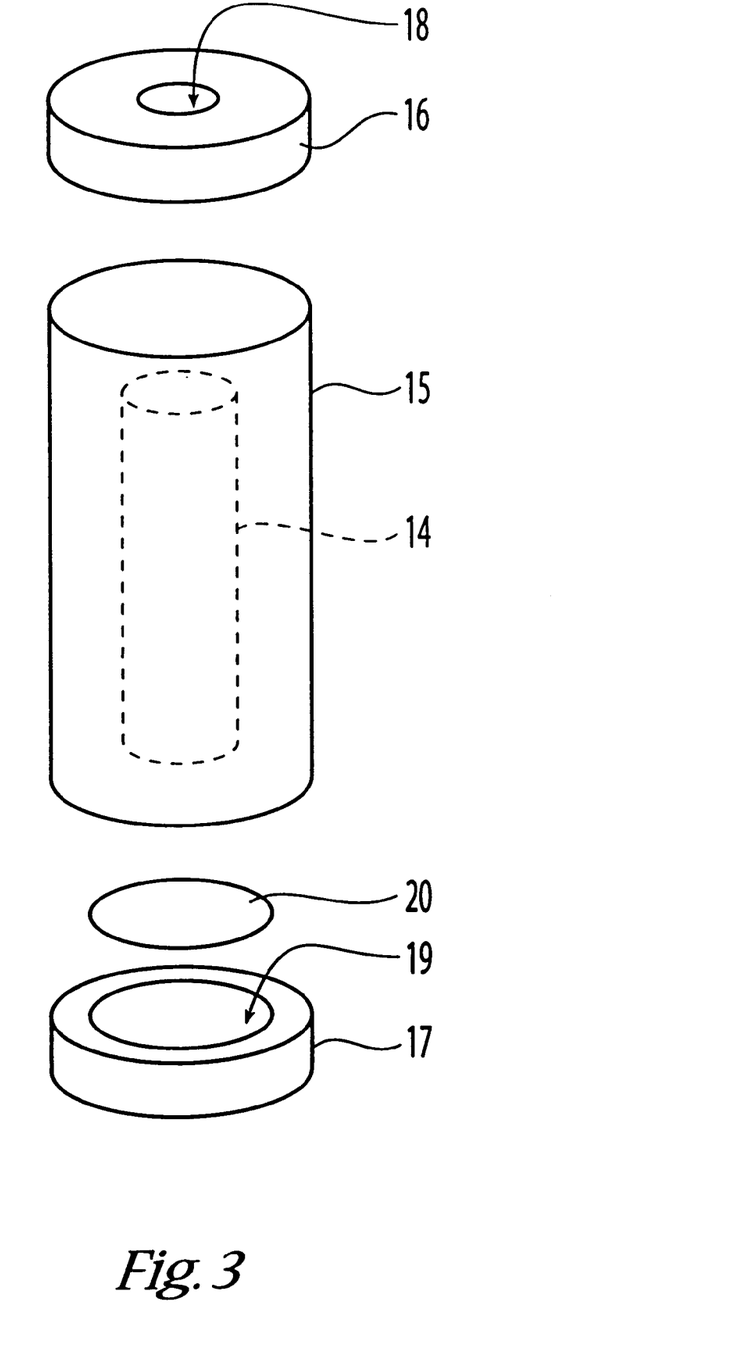
FIG. 3 is an exploded side view of the forming zone used in the process for manufacturing an implant according to the present invention.

The present invention is also directed at methods of manufacturing the implant of compacted microparticles. One embodiment of the method is described schematically in FIG. 2. The method involves filling the upper end (7) of a forming zone (6) with dry microparticles (8). The forming zone (6) comprises a vessel having an upper end (7) and a lower end (10). An exploded side view of the forming zone (6) is depicted in FIG. 3. The forming zone may be a die (14) that is, for example, cylindrical in shape with a central hole having a diameter that is the same as that of the finished product. The die (14) is maintained in a holder (15). The upper end of the holder (15) is adapted to receive a top cap (16). The lower end of the holder (15) is adapted to receive a bottom cap (17). The top cap (16) has a hole (18) which allows the introduction of microparticles (8) and fluid (9) into the die. The bottom cap also has a hole (19) that is closed with a seal (20) that does not allow microparticles to pass through but allows fluids and gases to pass through. After the microparticles (8) are added to the forming zone a suitable fluid (9), such as water, with or without excipients, is added to the microparticles (8) in the forming zone (6). The fluid is allowed to contact the microparticles for an amount of time that is sufficient to allow the fluid to evenly coat the surface of the microparticles. The fluid coats the surface of the microparticles as a result of natural forces such as gravity and/or capillary action. After the microparticles are evenly coated with the fluid a pressure (21) is applied to the upper end (7) of the forming zone (6) to compact the microparticles. The bottom cap (17) of the holder is then removed and the compacted microparticles are ejected under pressure (12) and dried (13).

The fluid is typically allowed to contact the microparticles for between about 1 second and 5 minutes, preferably for between about 10 seconds and 1 minute. Wetting the surface of the microparticles before applying the pressure improves adhesion of the compacted particles. Without wishing to be bound by theory it is believed that the fluid wets the surface of the microparticles and interacts with drug molecules present on the surface of the microparticle to increases adhesion of the microparticles.

Figure 4:
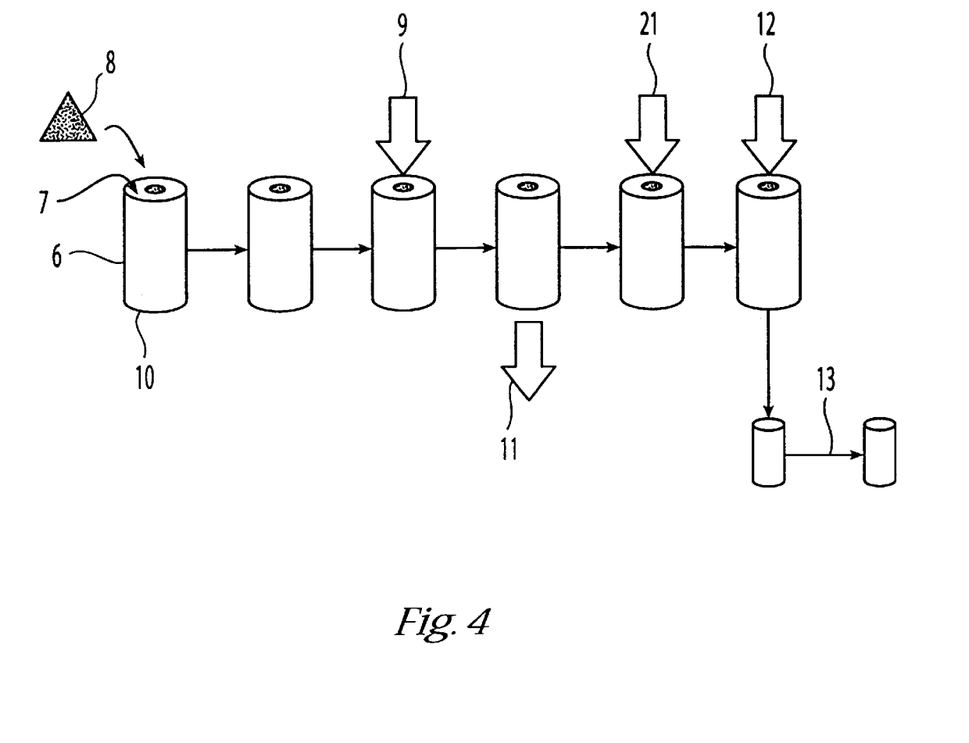
FIG. 4 is a schematic representation of a process for manufacturing an implant according to the present invention.

In a second embodiment of the invention, described in FIG. 4, the bottom cap (17) of the holder is closed with a seal (20) that allows fluids and gases, but not the microparticles to pass through. The microparticles (8) and a suitable fluid (9) are added to the forming zone and a vacuum (11) is applied to the lower end (10) of the forming zone (6) to create a reduced pressure. The reduced pressure helps evenly disperse the fluid on the surface of the microparticles. The reduced pressure is typically between about 2 and 50 inches of mercury, preferably between about 10 and 25 inches of mercury. After the microparticles are evenly coated with the fluid the vacuum is removed and a pressure (21) is applied to the upper end (7) of the forming zone (6) to compact the microparticles. The vacuum assists in coating the surface of the microparticles with the fluid. To assure that the microparticles are coated with the fluid the reduced pressure is removed before all of the fluid is withdrawn from the forming zone (6). The bottom cap (17) of the holder is then removed and the compacted microparticles are ejected under pressure (12) and dried (13).

The seal prevents the microparticles from exiting the forming zone especially when pressure is applied to the upper end (7) of the forming zone (6) to compact the microparticles. The seal may be any type of filter medium readily known to those of ordinary skill in the art. Typically, the seal is a paper filter. Other materials for the filter medium include, but are not limited to, cellulose acetate and nylon. Typically the filter medium is supported on a metal frit or mesh, for example, to prevent the filter medium from tearing when pressure is applied to the upper end (7) of the forming zone (6).

Figure 5:
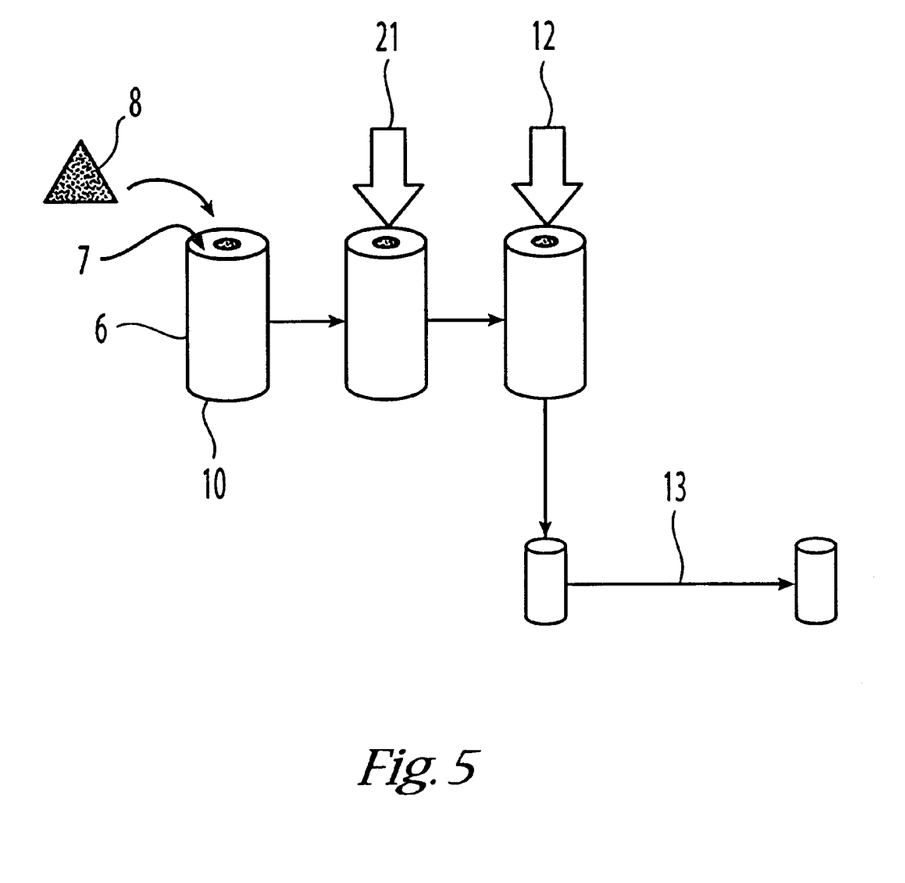
FIG. 5 is a schematic representation of a process for manufacturing an implant according to the present invention.

A third embodiment of the method is described schematically in FIG. 5. The method involves filling the upper end (7) of a forming zone (6) with microparticles (8). The microparticles (8), however, are added to the forming zone (6) as a wet granulate. The wet granulate is made by combining the microparticles (8) with a fluid. The hole (19) in the bottom cap (17) is closed with a seal (20) that does not allow microparticles, fluids, and gases to pass through. After the wet granulate is added to the forming zone a pressure (21) is applied to the upper end (7) of the forming zone (6) to compact the microparticles. The bottom cap (17) of the holder is then removed and the compacted microparticles are ejected under pressure (12) and dried (13).

The microparticles may be commercially available microparticles or may be prepared especially for the purpose of making the implant of the present invention. The microparticles may be prepared by any conventional method. These methods are well known to those or ordinary skill in the art and need not be discussed here.

The microparticles may be further mixed with additional additives before being placed into the forming zone. For example, the microparticles may be mixed with biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucuronic acid, gluconic acid, polysorbate, sodium acetate, sodium citrate, sodium phosphate, zinc stearate, aluminum stearate, magnesium stearate, sodium carbonate, sodium bicarbonate, sodium hydroxide, polyvinylpyrrolidones, polyethylene glycols, carboxymethyl celluloses, methyl celluloses, starch, and the like, or mixtures thereof. The additive(s), when present, is present in a amount of between about 0.05 to 75% (w/w) of the implant, preferably 0.5 to 50% (w/w) of the implant.

The volume of fluid added can be between about 20% and 200% (v/w) of the microparticles, preferably between about 25% and 100% (v/w), and more preferably between about 30% and 70% (v/w). The volume of fluid to be added to the microparticles in any of these embodiments is readily determined by adding incremental amounts of fluid to a known weight of dry microparticles with mixing. Fluid is continually added in small increments until a moist granulate or paste is formed that does not contain any excess free flowing liquid. The fluid can be any non-solvent of the polymer or mixture of non-solvents that is volatile. The fluid can be, for example, water, ethanol, methanol, heptane, or a mixture thereof. The fluid may also be a solution of one or more compounds dissolved in the solvent. For example, the solution may be an aqueous solution of mannitol, salts such as sodium chloride, polyethylene glycol, acids, bases, and the like. The preferred fluid is water.

The pressure (21) applied to the upper end (7) of the forming zone (6) may be between about 1 kg/cm² and 1,000 kg/cm², preferably between about 10 kg/cm² and 500 kg/cm². The pressure (21) is applied for between about 1 second and 10 minutes, preferably between about 10 seconds and 5 minutes. The pressure (21) may be applied by any means known to those of ordinary skill in the art. In one embodiment the hole (18) in the top cap (16) is adapted to receive a plunger and the microparticles are compressed using the plunger.

After the compact of microparticles is ejected from the forming zone it is dried to provide the implant. The compact of microparticles can be dried at a temperature of from about 0° C. to 80° C., preferably from about 15° C. to 40° C., and most preferably from about 20° C. to 30° C. The compact of microparticles can be dried at atmospheric pressure or under reduced pressure. In addition, the compact of microparticles can be dried in the presence of a desiccant such as, for example, phosphorous pentoxide ($P_2O_5$). Drying times can vary from about 1 hour to about 1 week.

By varying different parameters in the manufacturing process the rate of release of the drug over time, after administration, can be controlled. For example, the rate of release of the drug can be varied by changing the core loading; compacting pressure; particle size; or by including additives in the implant. Additives include, but are not limited to, hydrophobic, hydrophilic, swelling and solubilizing additives such as those described above.

For example, the process of the present invention provides control over how the microparticles are compacted together. Thus, the speed at which the implant disintegrates into individual particles of microparticles under the skin can be controlled. Similarly, various additives can influence the rate at which the implant disintegrates. Controlling the speed at which the compact disintegrates provides control over release of the active due to the burst. For example, if a higher compacting pressure is used a more compact implant will result, the implant will disintegrate more slowly and will exhibit less of a burst. High core loading is associated with a high burst, thus, decreasing the burst is advantageous in that it allows the administration of microparticles with a higher core loading of the drug. In fact, the present invention allows for the administration of microparticles that have a core loading in excess of 25% and even in excess of 50%. By controlling the burst the implants of the present invention permit large amounts of drug to be administered in small volumes. The process of the present invention provides a method for manufacturing implants wherein the rate of release of the drug can be accurately controlled.

EXAMPLES

The invention is further defined by reference to the following examples describing in detail the pharmaceutical implants of the present invention. The examples are representative and they should not be construed to limit the scope of the invention in any way.

Unless otherwise noted, pharmaceutical implants were prepared according to the method described schematically in FIG. 2. The implants were made of microparticles containing the peptide Teverelix. The microparticles were obtained by extrusion followed by grinding. Each microparticle contained 25 percent of Teverelix. 40 milligrams of microparticles were placed in a forming zone as depicted in FIG. 3 and 20 µL of water was added to the forming zone. A reduced pressure of 5 inches of mercury was used to evenly coat the microparticles with the water. The resulting pharmaceutical implant was about 1.2 cm in length and had a diameter of about 0.2 cm.

The pharmaceutical implants were placed in water or Ringer solution at 37° C. and the amount of Teverelix released was measured spectrophotometrically at 227 nm as a function of time. Disintegration times for the implants were evaluated by comparing the amount of Teverelix released from the implant to the amount of Teverelix released from non-compressed (control) microparticles. Rapid release of Teverelix indicates rapid disintegration of the pharmaceutical implant.

Effect of Particle Size on In Vitro Release of Teverelix

Figure 6:
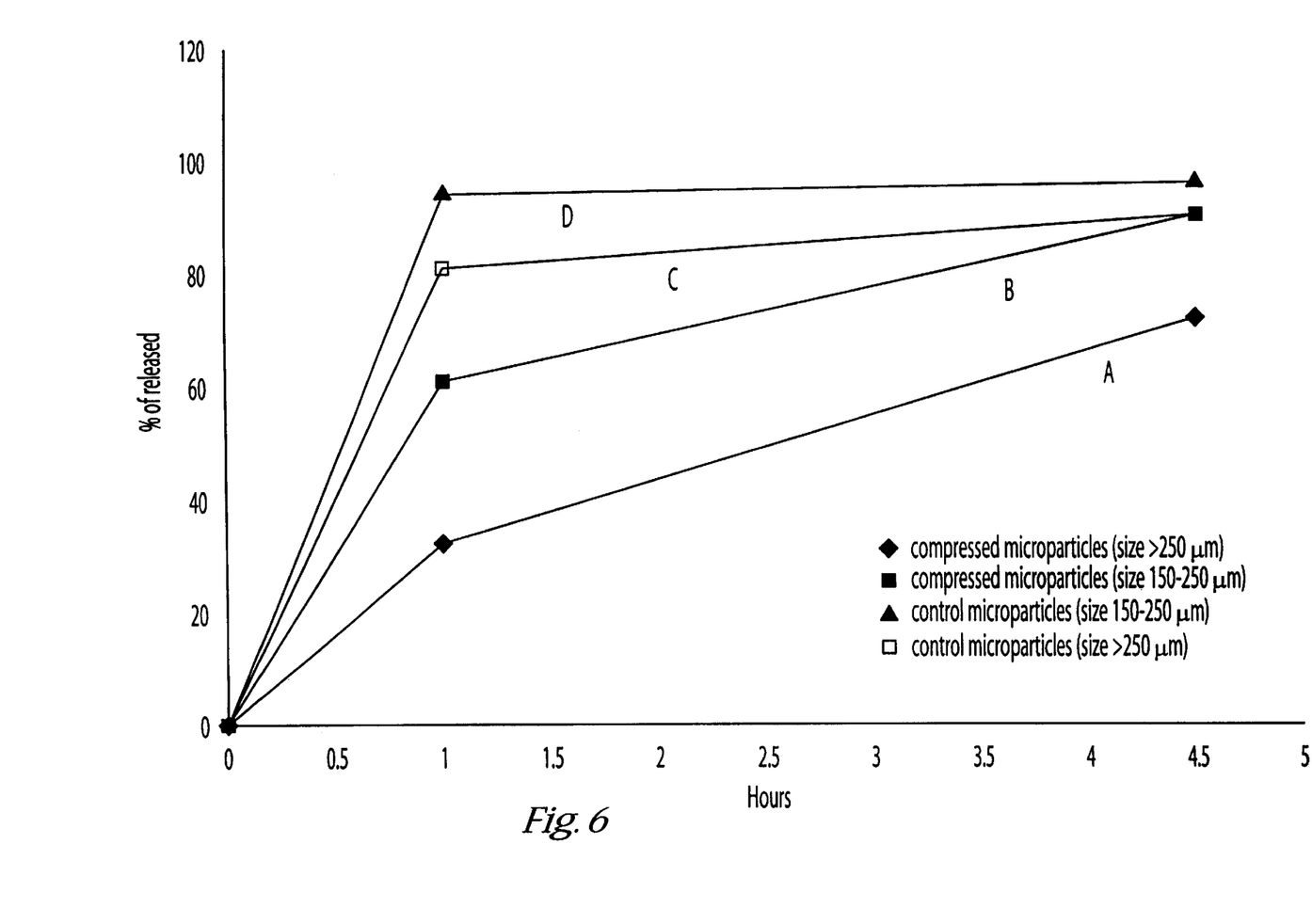
FIG. 6 is a graphical representation depicting how the size of the microparticles affects the rate of disintegration of an implant of the present invention.

FIG. 6 compares the release of Teverelix from compressed microparticles having different particle sizes. Rates of release were determined in water at 37° C. Line A shows the release of Teverelix from compressed microparticles having a size of greater than 250 µm. Line B shows the release of Teverelix from compressed microparticles having a size of between 150–250 µm. Lines C and D show the release of Teverelix from control microparticles, that is non-compressed microparticles, having a size of greater than 250 µm and a size between 150–250 µm, respectively.

FIG. 6 shows that the compressed microparticles of the present invention having a particle size greater than 250 µm are not broken down into particles after 4.5 hours. In contrast, a pharmaceutical implant having a smaller particle size of between 150–250 µm disintegrates more quickly, i.e., disintegration is essentially complete after 4.5 hours. Thus, the rate of disintegration of the pharmaceutical implant of the present invention can be varied by varying the size of the microparticles.

Effect of Additives on In Vitro Release of Teverelix

Figure 7:
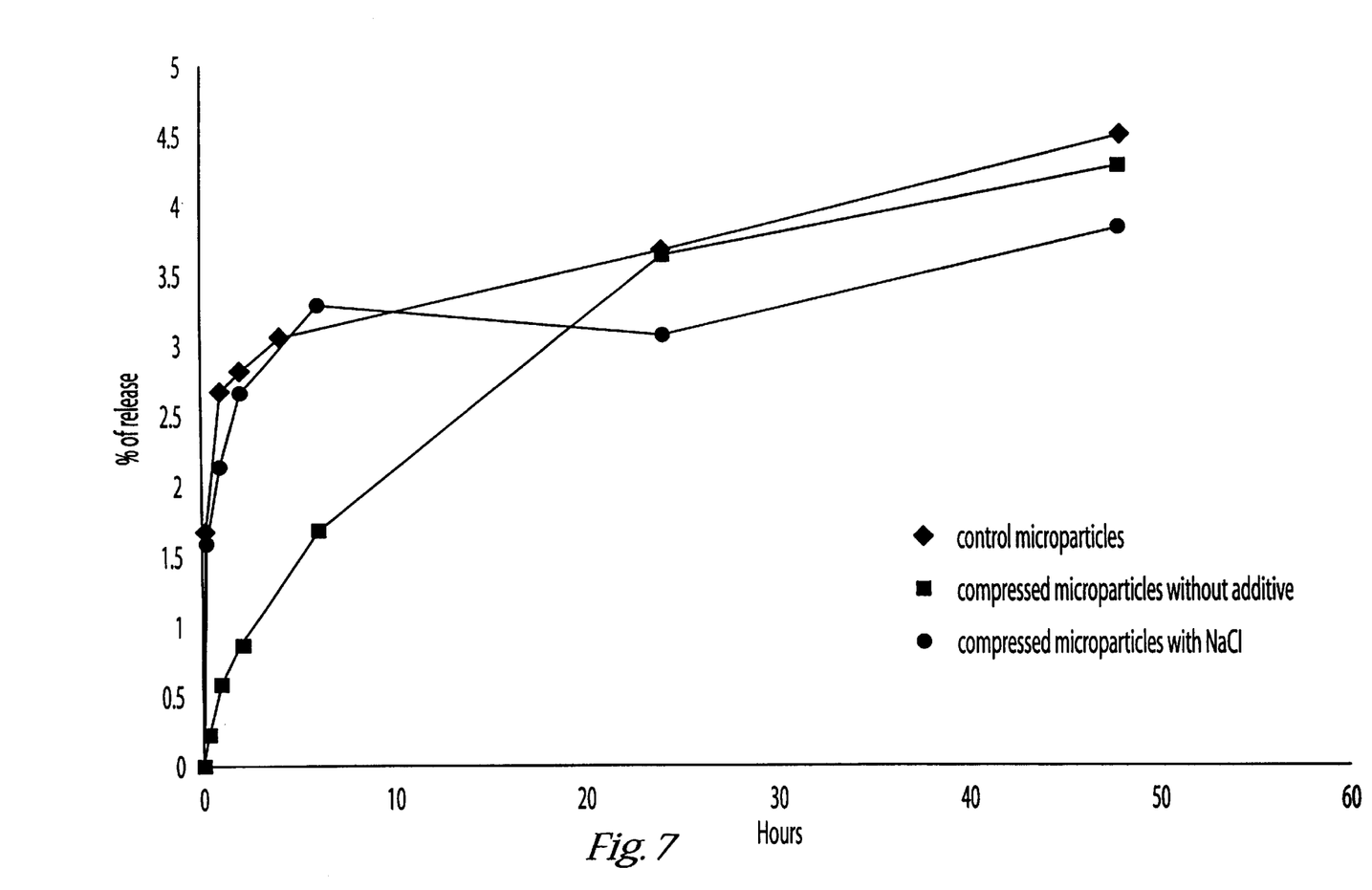
FIG. 7 is a graphical representation depicting how the addition of sodium chloride to an implant of the present invention affects disintegration of an implant.

FIG. 7 compares the release of Teverelix from compressed microparticles with and without the additive sodium chloride. Rates of release were determined in Ringer solution at 37° C. Sodium chloride was added to the pharmaceutical implants in an amount of 1 percent by weight. FIG.

7 shows that the addition of sodium chloride accelerates the rate of disintegration of the pharmaceutical implant.

Figure 8:
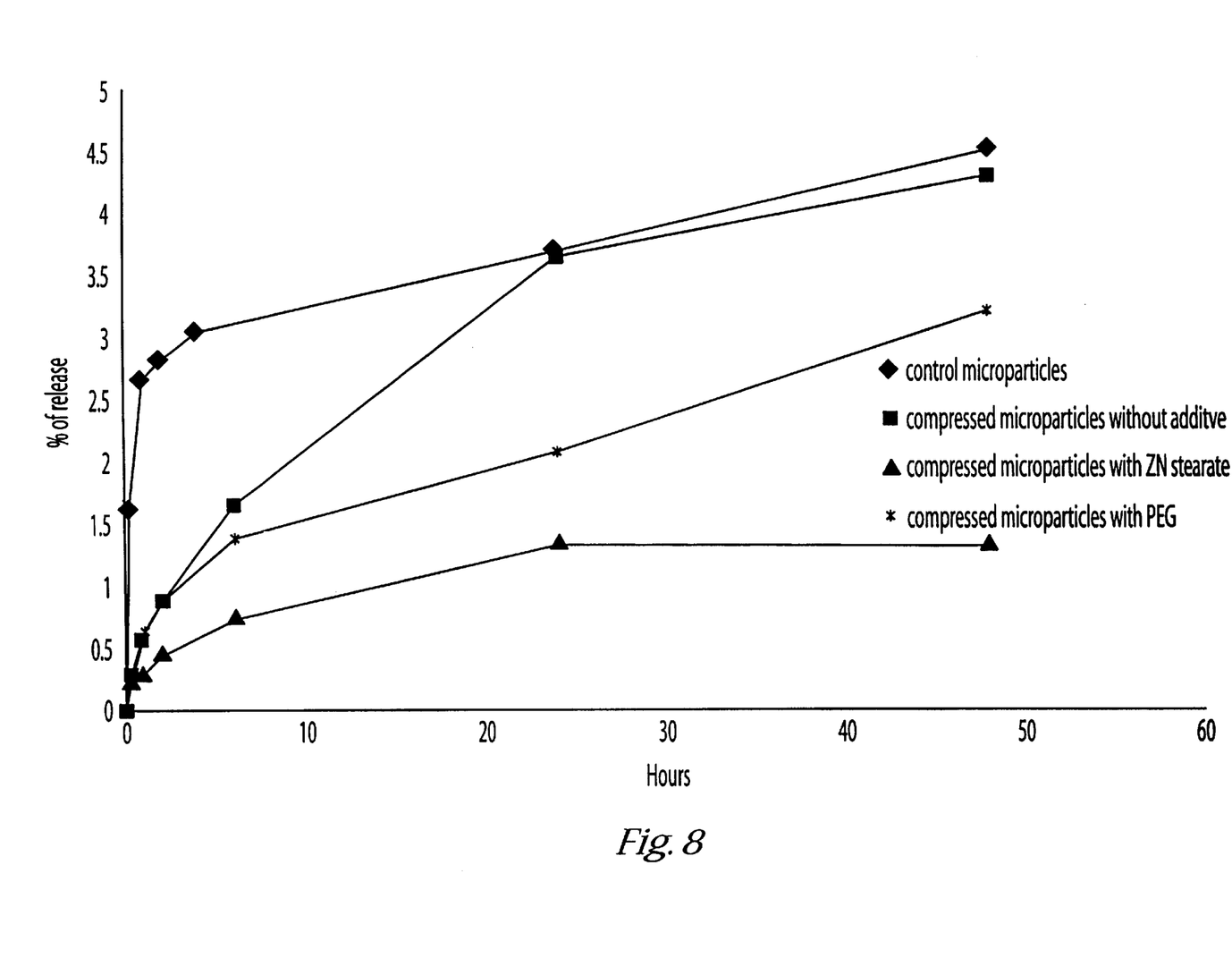
FIG. 8 is a graphical representation depicting how the addition of polyethylene glycol or zinc stearate to an implant of the present invention affects disintegration of an implant.

FIG. 8 compares the release of Teverelix from compressed microparticles with and without the additives polyethylene glycol (PEG) and zinc stearate. PEG and zinc stearate were added to the pharmaceutical implants in amounts of 1 percent by weight, respectively. FIG. 8 shows that the addition of PEG or zinc stearate inhibits the rate of disintegration of the pharmaceutical implant. Thus, by incorporating various additives into the pharmaceutical implants of the present invention the rate of disintegration of the implant can be increased or decreased.

Figure 9:
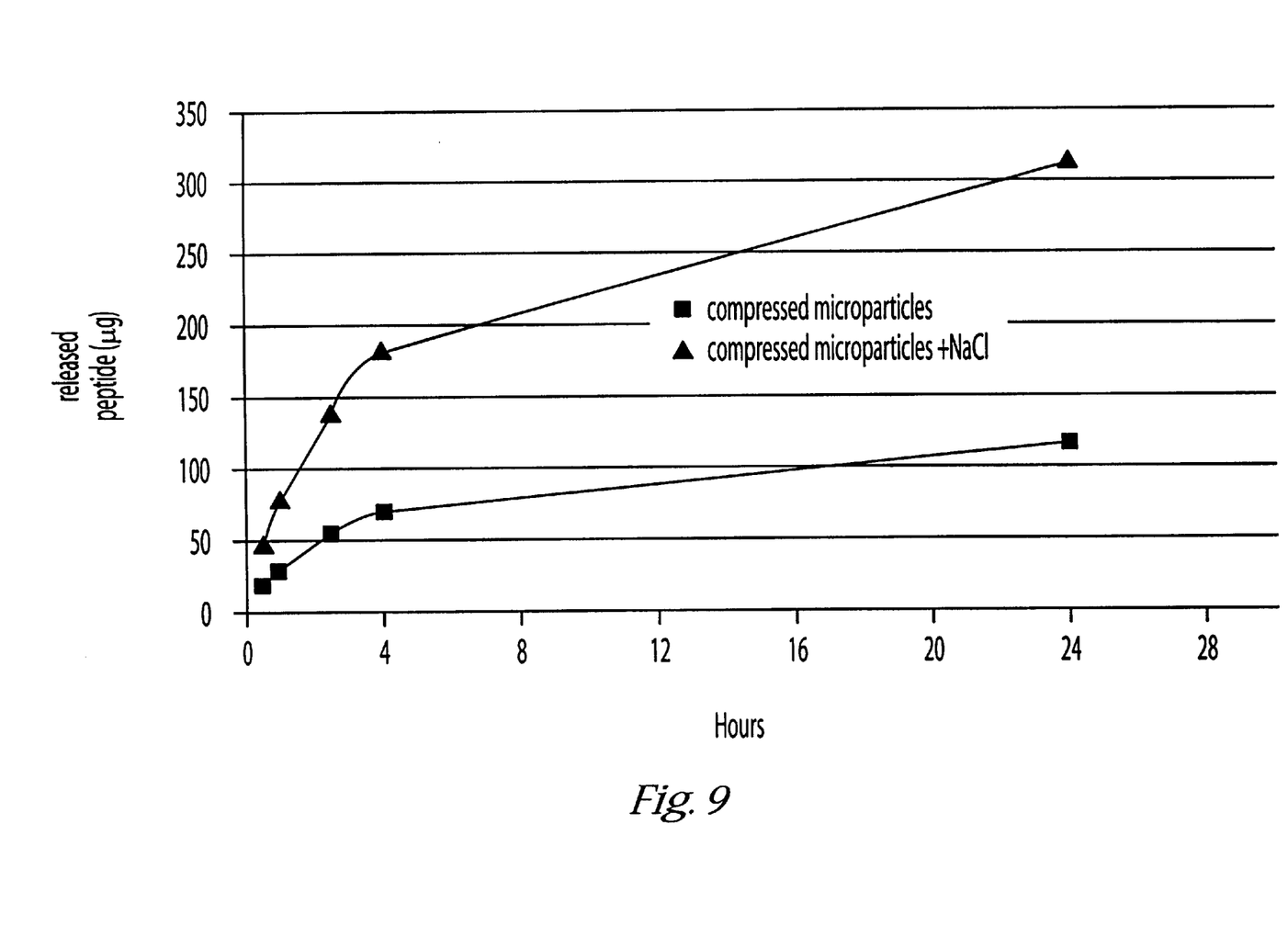
FIG. 9 is a graphical representation depicting how the addition of sodium chloride to an implant made by the process of the present invention depicted in FIG. 5 affects disintegration of an implant.

FIG. 9 also compares the release of Teverelix from compressed microparticles with and without the additive sodium chloride. Rates of release were determined in Ringer solution at 37° C. The microparticles used to generate the data in FIG. 9, however, were made according to the method described schematically in FIG. 5.

To prepare the microparticles 15 mg of microparticles each containing 25% percent by weight of Teverlix were combined with 5 mg of water to make a wet granulate. The wet granulate was placed in a forming zone as depicted in FIG. 3 and a pressure of 30 kg/cm² was applied for 10 seconds. The resulting pharmaceutical implant was about 0.5 cm in length and had a diameter of about 0.2 cm. Sodium chloride was added to the pharmaceutical implants in an amount of 5 percent. FIG. 9 again shows that the addition of sodium chloride accelerates the rate of disintegration of the pharmaceutical implant.

The invention described and claimed herein is not to be limited in scope by the specific embodiments herein disclosed, since these embodiments are intended as illustrations of several aspects of the invention. Any equivalent embodiments are intended to be within the scope of the invention. Indeed, various modifications of the invention in addition to those shown and described herein will become apparent to those skilled in the art from the foregoing description. Such modifications are also intended to fall within the scope of the appended claims.

What is claimed is:

1. A controlled-release, injectable pharmaceutical implant comprising microparticles that have a biodegradable polymer matrix and one or more drugs comprising a peptide dispersed therein, wherein the microparticles are sufficiently associated to maintain a predetermined shape of the implant without complete fusing of the polymer, adapted for injection to a subject and wherein the implant disintegrates into individual microparticles over time after injection.

2. The pharmaceutical implant of claim 1 wherein the amount of the drug is between about 0.5 to 95 percent (w/w) of the microparticles.

3. The pharmaceutical implant of claim 1 wherein the amount of the drug is between about 5 to 75 percent (w/w) of the microparticles.

4. The pharmaceutical implant of claim 1 wherein the biodegradable polymer is selected from the group consisting of polymers of lactic acid, glycolic acid, polyethylene glycols, poly(ortho esters), poly caprolactones, and copolymers thereof.

5. The pharmaceutical implant of claim 1 further comprising one or more additives.

6. The pharmaceutical implant of claim 5 wherein the one or more additives are selected from the group consisting of biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucuronic acid, gluconic acid, polysorbate, sodium acetate, sodium citrate, sodium phosphate, zinc stearate, aluminum stearate, magnesium stearate, sodium carbonate, sodium bicarbonate, sodium hydroxide, polyvinylpyrrolidones, polyethylene glycols, carboxymethyl celluloses, methyl celluloses, starch, and mixtures thereof.

7. The pharmaceutical implant of claim 1 wherein the microparticles have a particle size of 10 microns to about 1,000 microns.

8. The pharmaceutical implant of claim 1 wherein the implant is a sphere, a pellet, or a cylinder.

9. A controlled-release, injectable pharmaceutical implant comprising microparticles that have a biodegradable polymer matrix and one or more drugs dispersed therein, wherein the microparticles are sufficiently associated to maintain a predetermined shape of the implant without complete fusing of the polymer, adapted for injection to a subject and wherein the implant disintegrates into individual microparticles over time after injection, wherein the implant has a cylindrical shape, has a diameter of about 0.5 to 5 mm, and has a length of about 0.5 to 10 cm, and wherein the microparticles have a particle size of about 10 microns to about 1,000 microns.

10. A method for controllably releasing a drug in a subject comprising injecting to the subject a pharmaceutical implant comprising microparticles that have a biodegradable polymer matrix and one or more drugs dispersed therein, wherein the microparticles are sufficiently associated to maintain a predetermined shape of the implant without complete fusing of the polymer and wherein the implant disintegrates into individual microparticles over time after injection.

11. The method of claim 10 wherein the implant is administered intramuscularly or subcutaneously.

12. The method claim 11 wherein the implant is administered surgically or using an implantation device.

13. The method of claim 12 wherein the implantation device is pre-filled with the implant.

14. A method of preparing a pharmaceutical implant for controllably releasing a drug in a subject comprising the steps of:

placing microparticles that have a biodegradable polymer matrix and one or more drugs dispersed therein in a forming zone defined by a vessel having an upper end and a lower end, wherein the upper end has an opening to permit the microparticles and a fluid to be introduced into the forming zone, the lower end is covered with a seal that prevents the microparticles from exiting the forming zone but allows gases and fluids to exit the forming zone;

adding a fluid to the upper end of the forming zone in an amount sufficient to evenly coat the microparticles to increase adhesion of the microparticles;

applying a pressure to the upper end of the forming zone to compact the microparticles and sufficiently associate the microparticles so that they maintain the shape of the forming zone without complete fusing of the polymer;

removing the compacted microparticles from the forming zone in the shape of the implant; and drying the compacted microparticles to provide a pharmaceutical implant that disintegrates into individual microparticles over time after the implant is administered to a subject.

15. The method of claim 14 wherein the lower end of the forming zone is adapted to receive a vacuum and further comprising the step of applying a vacuum to the lower end of the forming zone, after the fluid is added, to evenly coat the microparticles with the fluid.

16. The method of claim 14 wherein the vacuum creates a reduced pressure of between about 2 and 50 inches of mercury.

17. The method of claim 14 further comprising combining the microparticles with one or more additives to form a mixture before placing the mixture in the forming zone.

18. The method of claim 17 wherein the additives are selected from the group consisting of biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucuronic acid, gluconic acid, polysorbate, sodium acetate, sodium citrate, sodium phosphate, zinc stearate, aluminum stearate, magnesium stearate, sodium carbonate, sodium bicarbonate, sodium hydroxide, polyvinylpyrrolidones, polyethylene glycols, carboxymethyl celluloses, methyl celluloses, starch, and mixtures thereof.

19. The method of claim 17 wherein the additive is present in an amount of between about 0.05 percent (w/w) and 75 percent (w/w) of the implant.

20. The method of claim 14 wherein the fluid is added in an amount of between about 20 percent (v/w) and 200 percent (v/w) of the weight of the microparticles.

21. The method of claim 14 wherein the fluid is one or more fluids selected from the group consisting of water, ethanol, methanol, and heptane.

22. The method of claim 14 further comprising adding a solute to the one or more fluids.

23. The method of claim 22 wherein the solute is selected from the group consisting of mannitol, salts, polyethylene glycol, acids, bases, and mixtures thereof.

24. The method of claim 14 wherein the compacted microparticles are dried at a temperature of between about 15° C. to 40° C.

25. The method of claim 24 further comprising drying the compacted microparticles under reduced pressure.

26. The method of claim 24 further comprising drying the compacted microparticles in the presence of a desiccant.

27. The method of claim 14 wherein the pressure is between about 1 kg/cm$^2$ and 1,000 kg/cm$^2$ and is applied for between about 1 second and 10 minutes.

28. The method of claim 14 wherein the upper end of the forming zone is adapted to receive a plunger and pressure is applied using the plunger.

29. A method of preparing a pharmaceutical implant for controllably releasing a drug in a subject comprising the steps of:

combining microparticles that have a biodegradable polymer matrix and one or more drugs dispersed therein with a fluid to form a wet granulate;

placing the wet granulate in a forming zone defined by a vessel having an upper end and a lower end, wherein the upper end permits the wet granulate to be introduced into the forming zone and the lower end prevents the microparticles from exiting the forming zone;

applying pressure to the upper end of the forming zone to compact the microparticles and sufficiently associate the microparticles so that they maintain the shape of the forming zone without complete fusing of the polymer;

removing the compacted microparticles from the forming zone in the shape of the implant; and drying the come acted microparticles to provide a pharmaceutical implant that disintegrates into individual microparticles over time after the implant is administered to a subject.

30. The method of claim 29 further comprising combining the wet granulate with one or more additives before placing the wet granulate in the forming zone.

31. The method of claim 30 wherein the additives are selected from the group consisting of biodegradable polymers, mannitol, dextrose, inositol, sorbitol, glucose, lactose, sucrose, sodium chloride, calcium chloride, amino acids, magnesium chloride, citric acid, acetic acid, malic acid, phosphoric acid, glucuronic acid, gluconic acid, polysorbate, sodium acetate, sodium citrate, sodium phosphate, zinc stearate, aluminum stearate, magnesium stearate, sodium carbonate, sodium bicarbonate, sodium hydroxide, polyvinylpyrrolidones, polyethylene glycols, carboxymethyl celluloses, methyl celluloses, starch, and mixtures thereof.

32. The method of claim 30 wherein the additive is present in an amount of between about 0.05 percent (w/w) and 75 percent (w/w) of the implant.

33. The method of claim 29 wherein the fluid is added in an amount of between about 20 percent (v/w) and 200 percent (v/w) of the weight of the microparticles.

34. The method of claim 29 wherein the fluid is one or more fluids selected from the group consisting of water, ethanol, methanol, and heptane.

35. The method of claim 29 further comprising adding a solute to the one or more fluids.

36. The method of claim 35 wherein the solute is selected from the group consisting of mannitol, salts, polyethylene glycol, acids, bases, and mixtures thereof.

37. The method of claim 29 wherein the pressure is between about 1 kg/cm$^2$ and 1,000 kg/cm$^2$ and is applied for between about 1 second and 10 minutes.

38. The method of claim 29 wherein the compacted microparticles are dried at a temperature of between about 15° C. to 40° C.

39. The method of claim 38 further comprising drying the compacted microparticles under reduced pressure.

40. The method of claim 38 further comprising drying the compacted microparticles in the presence of a desiccant.

41. The method of claim 29 wherein the upper end of the forming zone is adapted to receive a plunger and pressure is applied using a plunger.

* * * * *

UNITED STATES PATENT AND TRADEMARK OFFICE
CERTIFICATE OF CORRECTION

PATENT NO.    : 6,627,600 B2
DATED         : September 30, 2003
INVENTOR(S)   : Boutignon It is certified that error appears in the above-identified patent and that said Letters Patent is hereby corrected as shown below:

Column 16,
Line 7, change "drying the come acted microparticles" to -- drying the compacted microparticles --.

Signed and Sealed this

Twenty-fifth Day of November, 2003

JAMES E. ROGAN
*Director of the United States Patent and Trademark Office*